(12) United States Patent
Hue et al.

(10) Patent No.: US 8,520,898 B2
(45) Date of Patent: Aug. 27, 2013

(54) METHOD AND SYSTEM FOR DETERMINING A REGION OF INTEREST IN AN IMAGE

(75) Inventors: David Hue, Chatou (FR); Samia Ahiad, Villemomble (FR); Abdelaziz Bensrhair, Mont Saint Aignan (FR)

(73) Assignee: Valeo Vision, Bobigny (FR)

( * ) Notice: Subject to any disclaimer, the term of this patent is extended or adjusted under 35 U.S.C. 154(b) by 371 days.

(21) Appl. No.: 12/831,526

(22) Filed: Jul. 7, 2010

(65) Prior Publication Data

US 2011/0013839 A1    Jan. 20, 2011

(30) Foreign Application Priority Data

Jul. 8, 2009   (FR) ...................................... 09 03384

(51) Int. Cl.
   *G06K 9/00*          (2006.01)
(52) U.S. Cl.
   USPC ............ 382/104; 382/103; 382/173; 382/199
(58) Field of Classification Search
   None
   See application file for complete search history.

(56) References Cited

U.S. PATENT DOCUMENTS

| 2004/0057599 | A1* | 3/2004 | Okada et al. | ................... | 382/103 |
| 2009/0128309 | A1* | 5/2009 | Hue et al. | ................... | 340/425.5 |

OTHER PUBLICATIONS

Chang et al.; "Adaptive Image Region-Growing", IEEE Transactions on Image Processing, IEEE, Service Center, Piscataway, NJ, US LNKD-DOI:10.1109/83.336259, pp. 868-872. Nov. 1, 1994.

Cufi et al.; "A Concurrent Region Growing Algorithm Guided by Circumscribed Contours", Pattern Recognition, 2000. Proceedings. 15th International Conference on Sep. 3-7, 2000; [Proceedings of the International Conference on Pattern Recognition. (ICPR)], Los Alamitos, CA, USA, IEEE Comput. Soc., US LKND-DOI:10.1109/ICPR.2000.905369. Sep. 3, 2000.

Deriche; "Using Canny's Criteria to Derive a Recursively Implemented Optimal Edge Detector". International Journal of Computer Vision, pp. 167-187. 1987.

Fan et al.; "Edge Based Region Growing—A New Image Segmentation Method", 2004, Proceedings VRCAI 2004—ACM Siggraph International Conference on Virtual Reality Continuum and its Applications in Industry. 2004.

Hautière et al.; "Automatic Fog Detection and Estimation of Visibility Distance Through Use of an Onboard Camera", Machine Vision and Applications, Springer-Verlag, vol. 17, No. 1, pp. 8-20. Apr. 1, 2006.

Higgins et al.; "Symmetric Region Growing", IEEE Transactions on Image Processing, IEEE Service Center, Piscataway, NJ, US, vol. 12, No. 9, pp. 1007-1015. Sep. 1, 2003.

Hojjatoleslami et al.; "Region Growing: A New Approach", IEEE Transactions on Image Processing, IEEE Service Center, Piscataway, NJ, US, vol. 7, No. 7, pp. 1079-1084. Jul. 1, 1998.

(Continued)

*Primary Examiner* — Bhavesh Mehta
*Assistant Examiner* — Siamak Harandi
(74) *Attorney, Agent, or Firm* — Jacox, Meckstroth & Jenkins

(57) ABSTRACT

A system and method for determining a region of interest in an image, characterized in that it comprises the following steps: a plurality of lines $L_{i\ i=1,\ldots,n}$ formed by pixels is defined in the image; in each line $L_i$, a plurality of segments $S_{j\ j=1,\ldots,m}$ constituted by pixels is defined; a luminance level $NVG(S_j)$ is calculated for each segment $S_j$ based on the luminance of the pixels constituting this segment $S_j$; depending on this luminance level $NVG(S_j)$ the segment $S_j$ is selected or excluded from the region of interest; and the region of interest is obtained by amalgamating all the segments selected for each line.

26 Claims, 7 Drawing Sheets

(56) References Cited

OTHER PUBLICATIONS

Kaohler; "A Segmentation System Based on Thresholding. Graphical Models and Image Processing". 1981.

Kitasaka et al.; "A Method for Segmenting Bronchial Trees from 3D Chest X-Ray CT Images", Medical Image Computing and Computer-Assisted Intervention—MICCAI. 6th International Conference. Proceedings. Part II (Lecture Notes in Comput. Sci. vol. 2879). Springer-Verlag, Berlin, Germany, pp. 603-610. 2003.

Tremeau et al.; "A Region Growing and Merging Algorithm to Color Segmentation", Pattern Recognition, Elsevier, GB, vol. 30, No. 7, pp. 1191-1204. Jul. 1, 1997.

Yong et al.; "Mammographic Mass Detection by Adaptive Thresholding and Region Growing", International Journal of Imaging Systems and Technology, Wiley, USA, vol. 11, No. 5, pp. 340-346. 2000.

* cited by examiner

METHOD AND SYSTEM FOR DETERMINING A REGION OF INTEREST IN AN IMAGE

CROSS-REFERENCE TO RELATED APPLICATIONS

This application claims priority to French Application No. 0903384 filed Jul. 8, 2009, which application is incorporated herein by reference and made a part hereof.

BACKGROUND OF THE INVENTION

1. Field of the Invention

The present invention relates to a method and a system for determining a region of interest in an image.

It finds application particularly in the automotive industry with, for example, the detection of visibility distance in foggy weather.

2. Description of the Related Art

With the development of electronic technologies, sensors and means of processing, many improvements have been proposed to make driving vehicles more safe or comfortable. Some of these improvements rely on analyzing an image of the environment around the vehicle to adapt handling of the vehicle handling or to inform the driver. Such is the case, for example, with systems for determining a visibility distance. These systems in particular are directed to adjusting the lighting of the vehicle according to the visibility distance.

In the known way, these systems include acquisition of an image and determination of a region of interest in this image intended to be processed in real time. Determination of a region of interest aims to exclude from the image the elements which would disturb its processing. It also enables the area of the image which is the object of the processing to be limited and consequently the quantity of data to be processed to be reduced. Thus, it offers the possibility of reducing the time and resources required for processing.

In existing systems, a region of interest is determined by using a "region growing" method. According to this method, the luminance of each pixel is analyzed and compared with the luminance of the pixels which are adjacent to it. If the variation of luminance is less than a preset threshold, then the region of interest is extended to these adjacent pixels so as to define a homogeneous area, if not these pixels are excluded from the region of interest. This method is in particular described in the document "A segmentation system based on thresholding. Graphical Models and Image Processing" [Käohler, 1981].

This method of region growing requires the luminance of each pixel to be determined and compared with the pixels which are adjacent to it. This method thus involves a considerable processing effort. It is consequently either not very robust, and does not then allow non-relevant elements to be removed from the region of interest, or extravagant in terms of computing time and use of resources. In practice, it has proven to be not very suitable for motor vehicles since this type of application requires rapid and reliable determination of the region of interest, at the same time limiting the cost price.

What is needed, therefore, is an improved approach for precisely delivering a region of interest in an image.

SUMMARY OF THE INVENTION

The aim of the present invention is to provide a method for precisely determining a region of interest in an image while consuming fewer resources in terms of processing.

For this purpose, a method for determining a region of interest in an image according to the invention is proposed, comprising the following steps:

a plurality of lines $L_{i\ i=1,\ldots,n}$ formed by pixels is defined in the image;

for each line $L_i$, a plurality of segments $S_{j\ j=1,\ldots,m}$ constituted by pixels is defined;

a luminance level $NVG(S_j)$ is calculated for each segment $S_j$ based on the luminance of each pixel constituting this segment $S_j$;

depending on this luminance level $NVG(S_j)$ the segment $S_j$ is selected or excluded from the region of interest; and the region of interest is obtained by amalgamating all the segments selected for each line.

Thus, one embodiment of the invention is based on the luminance of the segments, without discrimination of pixels based on the luminance of each pixel. Thus, it does not impose vicinity constraints on each pixel unlike the known methods. It consequently enables the resources required for processing the image to be substantially limited. In addition, being based on selection of segments according to their luminance level, one embodiment of the invention enables the elements of the image which induce inhomogeneities to be excluded.

Thus, a homogeneous region of interest is determined in a rapid manner and/or without requiring complex and costly means of processing.

In addition, the method according to the invention will be able to offer, optionally, at least one of the following features:

the luminance level $NVG(S_j)$ is an average luminance level $NVGaverage(S_j)$ corresponding to the average of the luminances of each of the pixels of this segment $S_j$;

it is determined if the average luminance level $NVGaverage(S_j)$ of this segment is comprised in the interval [$NVGaverage(L_{i-1})-S$; $NVGaverage(L_{i-1})+S'$], with S and S' being preset thresholds and $NVGaverage(L_{i-1})$ being the luminance level of one or more other adjacent lines;

if $NVGaverage(S_j)$ is comprised in this interval, then the segment $S_j$ is selected; and if $NVGaverage(S_j)$ is not comprised in this interval, then this segment $S_j$ is excluded from the region of interest.

Advantageously, it is proposed that the luminance level $NVGaverage(L_{i-1})$ corresponds to the average luminance level of one or more other adjacent lines.

In a preferred way, the difference is determined by comparing the average luminance level $NVGaverage(S_j)$ of the segment considered and the average luminance $NVGaverage(L_{i-1})$ of only one of the adjacent lines.

For example, only the average luminance $NVGaverage(L_{i-1})$ of the preceding line $L_{i-1}$ is analyzed and compared with the segment considered. This enables homogeneous regions to be detected and regions having a progressive degradation of contrast to be retained while limiting the resources required for processing.

Thus, according to the invention, the selection of a segment depends on the average luminance of an adjacent line. This selection thus does not depend exclusively on one preset parameter. This means that the invention adapts automatically depending on the ambient luminosity. Consequently, the invention improves detection of homogeneous regions, whatever the environment outside the vehicle.

This has proven particularly advantageous since current methods rely on preset thresholds of growth. However, for application to a motor vehicle, it is necessary to be able to identify a homogeneous region, whatever the type of road or whatever the ambient luminosity. Current methods, unlike the invention, do not necessarily allow a homogeneous region to be detected in a wide range of driving environments.

Moreover, in existing systems, the region growing method is often coupled with a contour detecting method. The function of the latter is to exclude from the image pixels belonging to non-homogeneous areas corresponding to specific objects of the image, such as vehicles, road marking lines, trees etc. However, the contour detecting methods do not allow objects, which appear blurred on the image because of fog or lack of luminosity, to be detected for example. These objects are then not detected. They are integrated in the region of interest and therefore disturb the luminance profile. Consequently, they induce inaccuracy when the visibility distance is calculated.

With the method according to the invention, the choice of thresholds enables segments with progressive degradation in the contrast of the image to be retained in the region of interest, while excluding textures blurred by fog and representing objects such as trees, shadows, vehicles etc.

In contrast to the known methods, the invention consequently enables homogeneous areas to be determined by eliminating objects even if they appear blurred on the image.

Alternatively, for all or part of the image, only the segment having the highest average grey scale NVGaverage($S_j$) is retained for each line $L_i$. Advantageously, this segment selection is only carried out for the area corresponding to the sky. This area generally has the highest grey scale.

The definition of each segment $S_j$ of a line $L_i$ comprises the following steps: a pixel of the line $L_i$ is considered, the segment $S_j$ is constituted by incrementing this pixel of the pixels that are consecutive and pertaining to this same line $L_i$ until a predetermined maximum number of pixels is reached.

Thus, to define the segments, one is not concerned with comparing the luminance of each pixel with the luminance of the pixels which are adjacent to it. The segments are defined without imposing any vicinity constraint with regard to the pixels. The segments are thus defined in a particularly easy way without requiring large resources in terms of processing.

Advantageously, prior to defining each segment $S_j$, of a line $L_i$, pixels forming contours are identified by a contour detecting method and only the pixel preceding the pixel corresponding to the contour forming a segment end is considered. This contour pixel is not integrated in the segment that is created.

Thus, the pixels associated with contours are eliminated. This step prior to defining the segments enables the segment ends to be imposed on the borders of each contour that is detected. Thus, the objects which disturb the homogeneity of the region of interest are excluded. In addition, the processing that is carried out is reduced since the pixels forming a contour are removed from the segments and are not analyzed.

The segment $S_j$ is excluded from the region of interest if the length of this segment $S_j$ is less than a preset minimum length.

A search window, inside which the plurality of lines $L_i$ is defined, is isolated in the image. Thus, a part of the elements which degrade the homogeneity of the area to be processed is eliminated. In addition, the surface of the image which is the object of the processing aiming to determine the region of interest and the resources required for processing are reduced.

It is considered that an incremented pixel forms a segment end when it corresponds to an edge of the search window. Definition of the segments thus takes into account the limits of the search window. This window defines and thus imposes segment ends.

In a preferred way the lines are horizontal. This has proved to be advantageous in an application aimed, for example, at determining a horizon line with calculation of a visibility distance being the final purpose. Vertical or oblique lines can also be provided.

The search window is segmented into a plurality of areas and specific rules concerning the definition of the segments $S_j$ and/or of the lines $L_i$ are allotted to each area.

Thus, rules for defining segments which depend on the area considered are applied. For example, it is proposed that the minimum and/or maximum size of the segments is varied according to the area considered. The more segments a line comprises, the greater the resources required for processing. The resources can then be concentrated on the critical areas in order to optimize allocation of resources for processing.

When selection of a segment relies on a comparison between a threshold and the difference between the average luminance level NVGaverage($S_j$) of this segment and the average luminance level of the amalgamated segments NVGaverage($L_{i-1}$) for one or more other adjacent lines, a specific threshold can also be allotted to each area.

This enables selection of the segments and their incorporation into the region of interest to be modulated according to the area considered. Depending on the thresholds, the method can thus be very selective, that is to say, so that objects blurred by fog, such as trees or shadows, are not retained in the region of interest, while it is less selective for areas where the probability of encountering these objects is low.

The search window comprises at least one first area and one second area respectively positioned horizontally around a first and a second vanishing point of the image. In the case of automotive application, the areas are thus positioned around directions which the vehicle is likely to take.

Preferably, the first and second areas respectively define a lower area and an upper area of the search window.

Advantageously, the method is implemented in a motor vehicle and at least one vanishing point is determined from a system for detecting a vanishing point based on a steering wheel angle of the vehicle and/or from data generated by a navigation system and/or from a system for detecting road marking lines.

Thus, a first lower area can be formed centered around the vanishing point defined according to methods known by the person skilled in the art. This area corresponds to the immediate vicinity of the vehicle. A second upper area can also be formed centered around a second vanishing point defined by a steering wheel angle of the vehicle and/or based on data generated by a navigation system and/or from a system for detecting road marking lines.

Preferably the search window comprises a third area defined so as to ensure continuity between the first and second areas.

Preferably the search window is segmented so that the third area corresponds in the image to a transition between the road and the sky. The three areas are thus defined so that the horizon line is contained in the intermediate area.

Rules are applied to the areas of the search window so that the size of the segments in the third area is less than that of the segments in the first and/or the second area. Thus, more processing resources are allocated to the intermediate area. It is, in fact, in this area that the horizon line should be detected. Consequently, determining the region of interest of this area must be particularly precise.

In order to obtain optimum precision, the method according to the invention is applied to each line of the image or of the search window. To limit the resources required for processing, this method can be applied to all the lines of only one or certain areas. The critical areas will then take priority. This method can again be applied to only some of the lines of the image, of the search window or of an area.

Advantageously the limits between the areas of the search window are positioned vertically according to data relating to pitching of the vehicle or so that the third area is vertically centered around a vanishing point of the image.

The region of interest obtained is amalgamated with a region determined according to another method for determining a region of interest. Thus, the region of interest obtained with the method according to the invention can be confirmed or enhanced.

Within the framework of the invention, a method for evaluating a visibility distance is proposed. According to this method, a region of interest is determined by implementing the method according to any one of the preceding features, a luminance level is determined for a plurality of lines in this region of interest, a luminance profile is deduced therefrom, an inflection point is identified on this luminance profile and a visibility distance is deduced from this inflection point. Advantageously the luminance level corresponds to an average luminance level for this plurality of lines.

Within the framework of the invention, a system is also proposed for determining a region of interest in an image, comprising a device for acquiring an image and a means of processing arranged to implement the method according to any one of the preceding features.

In addition, the invention relates to a vehicle comprising a system according to the preceding paragraph.

According to another object of the invention, a computer program package is provided comprising one or more sequences of executable instructions by a data processor, the execution of the sequences of instructions allowing one of the methods according to any one of the preceding features to be implemented.

According to another object of the invention, a system is provided for aiding a driver to drive a road vehicle using method for determining a region of interest in an image, this method being implemented in a road vehicle, the method comprising the following steps: means for defining a plurality of lines $L_{i\ i=1,\ldots,n}$ formed by pixels is defined in the image; means for defining in each line $L_i$, a plurality of segments $S_{j\ j=1,\ldots,m}$ constituted by pixels; means for collecting a luminance level $NVG(S_j)$ for each segment $S_j$ based on the luminance of the pixels constituting this segment $S_j$; means for selecting or excluding the segment $S_j$ from the region of interest in response to this luminance level $NVG(Sj)$; and means for amalgamating all the segments selected for each line to obtain the region of interest.

Other features, aims and advantages of this invention will appear upon reading the following detailed description, and with reference to the appended drawings, given as non restrictive examples, wherein:

BRIEF DESCRIPTION OF THE ACCOMPANYING DRAWINGS

FIG. 1 is a diagram illustrating the various steps of an exemplary embodiment of the invention for determining a visibility distance;

FIGS. 2*a* and 2*b* are examples of determining, respectively, relevant and non-relevant regions of interest;

FIG. 3 schematizes the various steps of an example for determining a region of interest according to the invention;

FIG. 4*a* illustrates an example of segmenting according to the invention a search window into a plurality of areas in a situation of driving in a straight line;

FIG. 4*b* illustrates an example of segmenting according to the invention a search window into a plurality of areas in a situation of driving around a curve;

DETAILED DESCRIPTION OF THE PREFERRED EMBODIMENTS

With reference to FIGS. 1 to 8, exemplary embodiments of the invention for determining a region of interest are illustrated. In these examples, determination of a region of interest has as an application the definition of a visibility distance particularly in foggy weather. Calculation of the visibility distance enables, for example, a motorist to be provided with a maximum driving distance or a minimum safety distance to be respected. This application of detecting a visibility distance constitutes an example allowing the invention to be clearly understood but does not limit it in any way. The method for defining a region of interest according to one embodiment of the invention can, in fact, be applied to other applications, such as for example identification of the edges of roads by only analyzing data from the road when the road line markings are no longer present. Another example is the use of the method for extraction from the road in order to detect vehicles or road signs.

Figure 1:
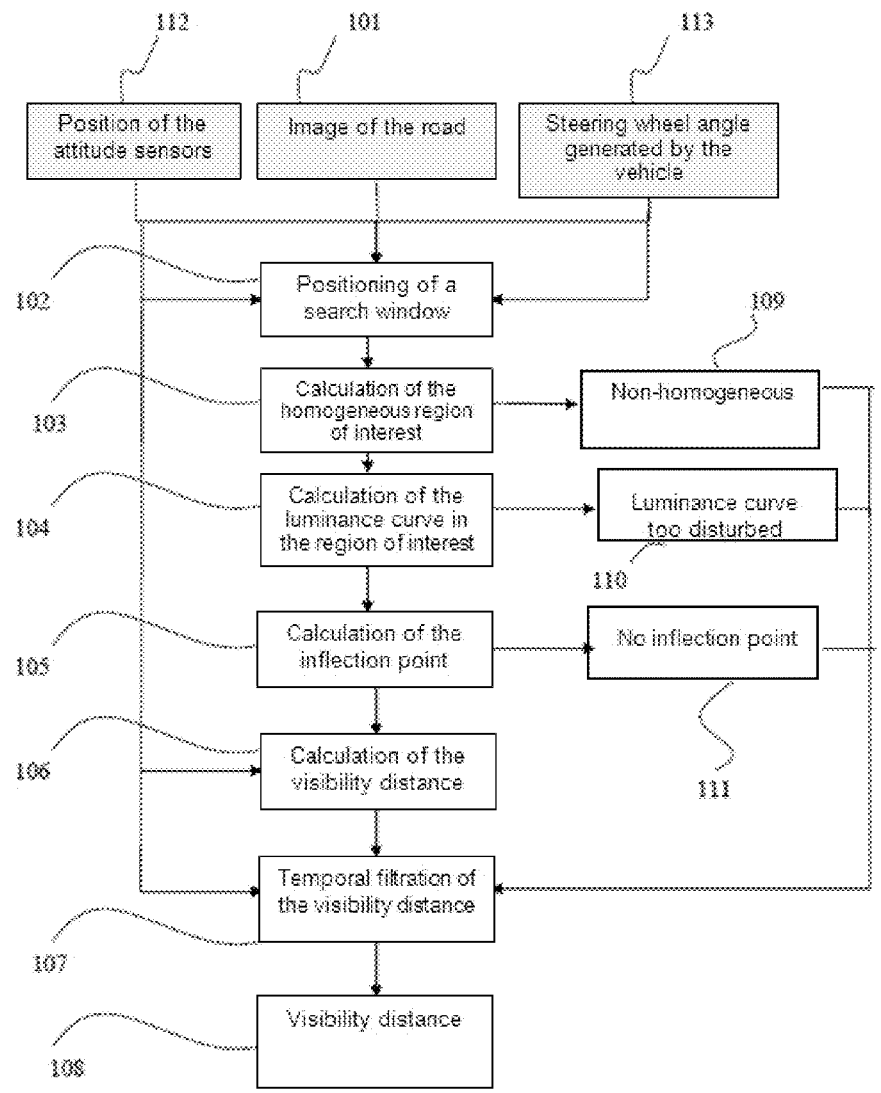

Evaluation of the visibility distance for example utilizes the steps illustrated in FIG. 1.

An image of the environment situated in front of a vehicle is acquired (step 101).

A region of interest is determined in the image. Advantageously, a search window, inside which the processing necessary for determining the region of interest is carried out, is positioned in the image (step 102). Determination of the region of interest (step 103) will be detailed below.

A grey scale or luminance profile curve is determined in the region of interest (step 104).

This curve is analyzed to determine the relevant inflection point (step 105).

Based on the position of the inflection point in the image and the position of the attitude sensors, the visibility distance is deduced therefrom by virtue of Koschmieder's law (step 106). For this purpose, reference can be made to Nicolas Hautière's theory and the article: "Automatic fog detection and estimation of visibility through [the use] of an onboard camera" published in the review "Machine vision and application" Springer-Verlag, BE, vol. 17, No. dated 1 Apr. 2006.

Advantageously, this method can be improved by using data based on the steering wheel angle and/or data generated by a navigation system and/or data resulting from detection of road markings and/or again from data resulting from attitude sensors (steps 112,113) in order to position the search window. This point will also be detailed below.

In addition, temporal filtering can also be carried out in order to determine the visibility distance more precisely (107, 108). For this purpose, a Kalman filter is used, for example, with the aim of temporally filtering the visibility distance data and also of predicting a visibility distance that has not been calculated. Indeed, it is possible that for one image the visibility distance is not calculated due to various reasons: non homogeneous region of interest (109), luminance curve too disturbed (110), no inflection point found (111). In this case, the algorithm used (the Kalman filter for example) predicts the visibility distance based on the preceding values and using the position of the attitude sensors.

Thus, if the steps, consisting in determining the region of interest (step 103) to calculate the luminance curve (step 104) and to deduce the inflection point (step 105), are not carried out successfully, then only the visibility distance is predicted (step 107).

Evaluation of the visibility distance is directly determined by the relevance of the luminance profile. The latter closely depends on the homogeneity of the region of interest.

Figure 2A:
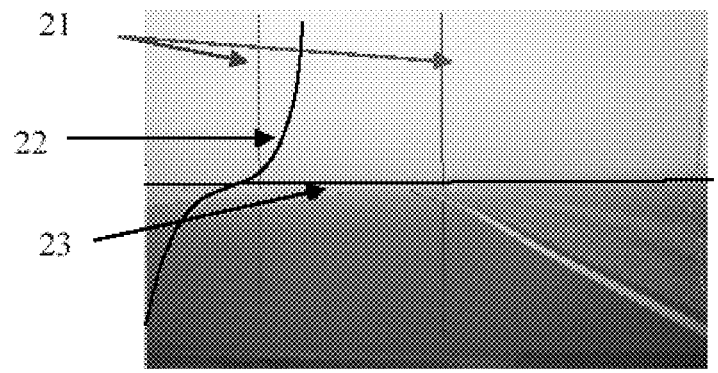

FIG. 2a is a photograph of an environment situated in front of the vehicle and includes few details. The region of interest delimited by the edges 21, 21 is homogeneous. This figure includes a luminance profile 22 having a substantially "S" shape with only one inflection point. Determination of the horizon line and the visibility distance are then possible and precise.

Figure 2B:
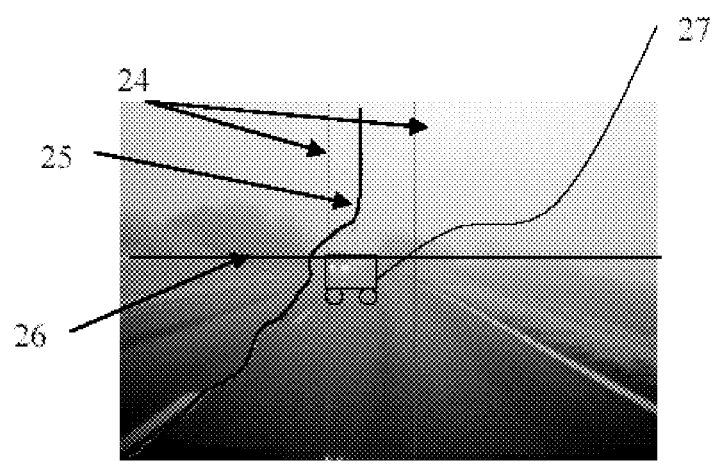

FIG. 2b illustrates an evaluation of the visibility distance using an existing method of region growing. The environment situated in front of the vehicle includes objects such as a vehicle 27 approaching in the opposite direction, trees etc. The region of interest retained according to the known method is delimited by the edges 24, 24 and includes these objects. This retained region of interest is thus not homogeneous. The luminance profile 25 is disturbed by these objects being taken into account. The horizon line 26 and the visibility distance are then incorrect.

As indicated previously, the invention proposes a method for determining a homogeneous region of interest, while limiting the resources required for processing.

A preferred embodiment of the invention will now be detailed with reference to FIGS. 3 to 7.

Figure 3:
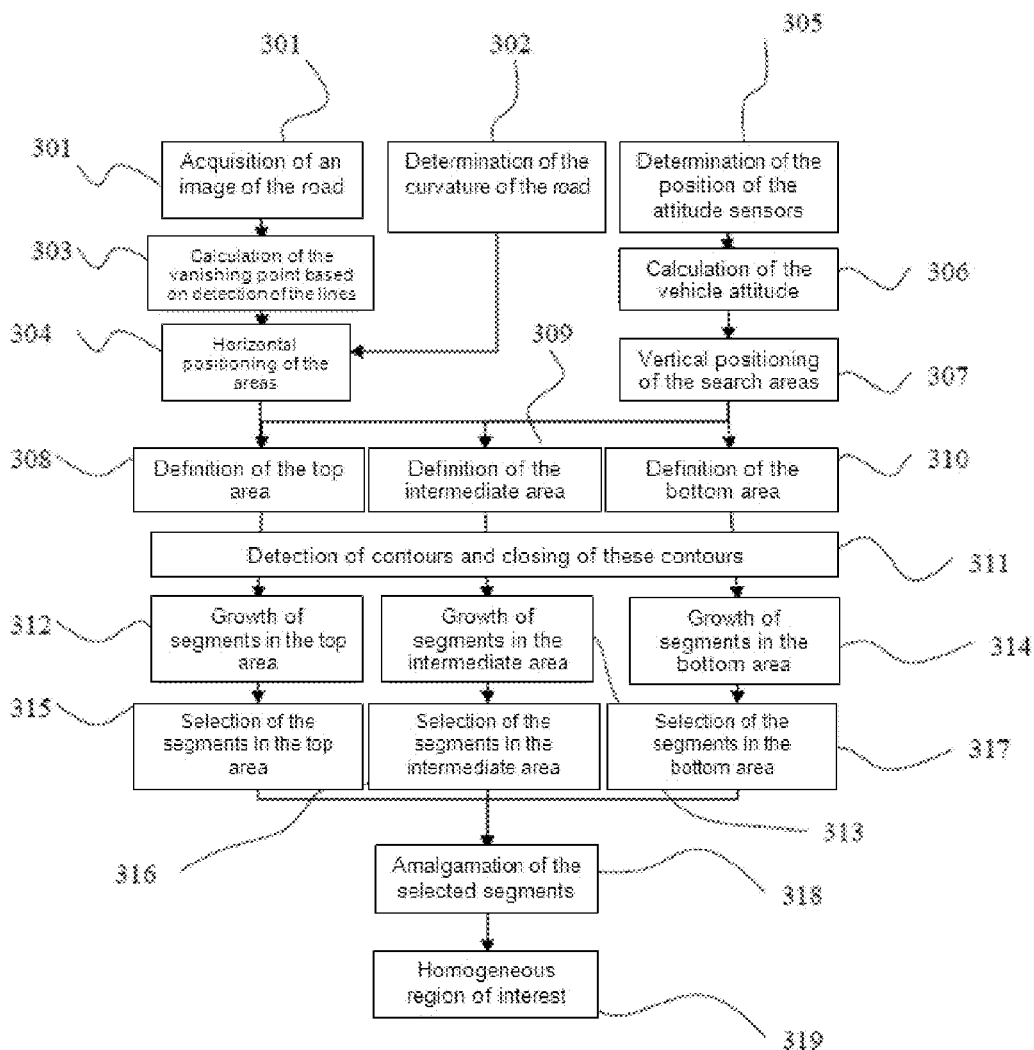

As illustrated by the diagram in FIG. 3, in the course of a first step (step 301—FIG. 3), an image is captured and a search window is selected in the image. Preferably, the search window extends from the top to the bottom of the image. It thus forms a band in the image. It covers heterogeneous areas around the grey scale average and various horizontal lines around the objects which it includes.

Thus, the top of the image corresponds to the sky. The top of the image therefore has a higher grey scale average compared to the remainder of the image. Objects that can usually be found in the top of the image are trees, lamp posts, bridges etc.

The bottom of the image corresponds to the road and the immediate surroundings of the vehicle. The bottom of the image therefore has a low grey scale average compared to the remainder of the image. The objects which can usually be found in the bottom of the image are road markings, vehicles being followed or approaching in the opposite direction, pedestrians or any object lying on the ground.

The middle of the image corresponds to an intermediate area ensuring a transition between the areas mentioned above and forming the top and bottom of the image. It is in this intermediate area that the inflection point will generally be sought in order to evaluate the visibility distance.

The search window is segmented into a plurality of areas. Advantageously, this segmentation comprises three areas. A first area corresponds to the top of the image, a second area corresponds to the bottom of the image and a third area corresponds to the intermediate area (steps 304, 308, 309, 310—FIG. 3).

Figure 4A:
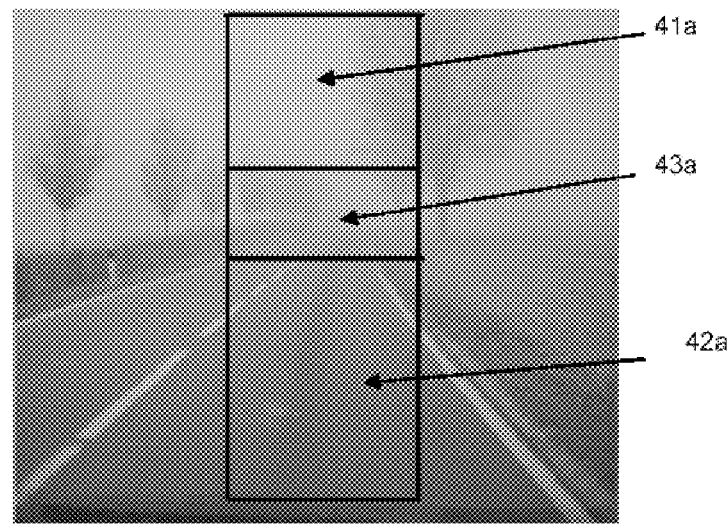

An example of segmenting the search window into three areas 41a, 42a, 43a is illustrated in FIG. 4a.

In a particularly advantageous way, the segmenting of the window and the positioning of the areas are adjusted according to data relating to the environment of the vehicle and/or the driving situation. For example, an area can be positioned according to a vanishing point of the image and/or a steering wheel angle based on data of the vehicle and/or data generated by a navigation system and reflecting the shape of the road and/or resulting from a system for detecting road markings and/or data relating to pitching of the vehicle etc. (steps 302, 303, 306, 307—FIG. 3). This positioning of the areas can be horizontal and/or vertical.

Figure 4B:
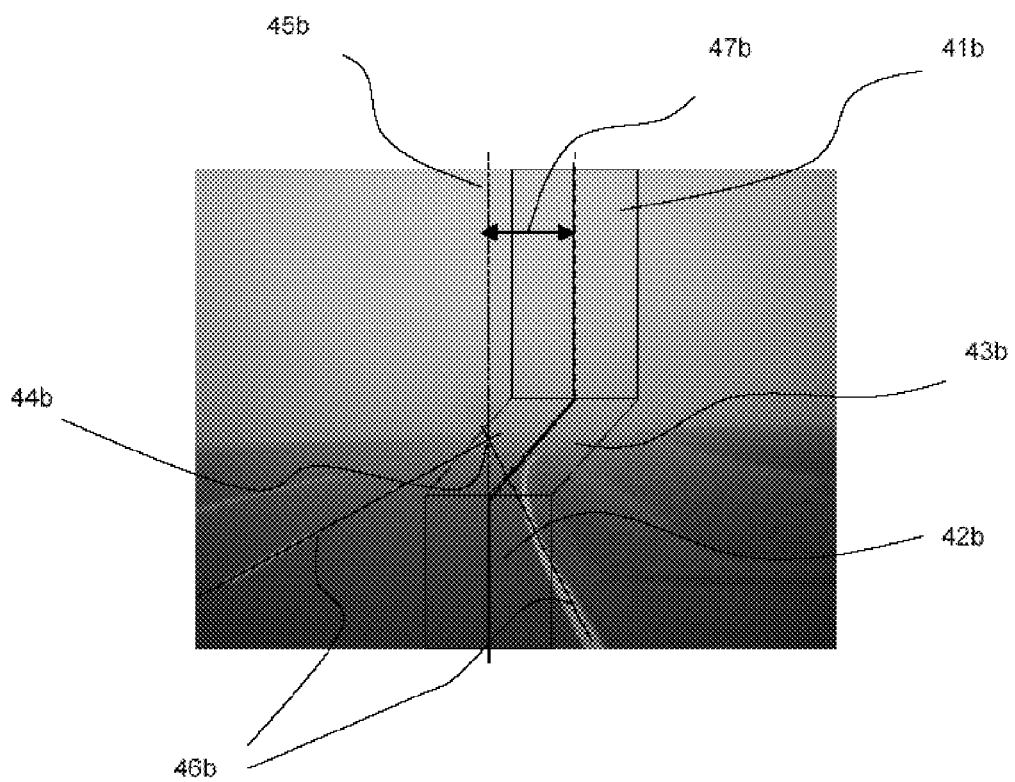

FIG. 4b illustrates an example of a search window in which the positioning of certain areas depends on the environment of the vehicle and/or the driving situations. In this example, the first area 41b corresponds to the top of the search window. It is centered horizontally around a vanishing point in a straight line. Methods known by the person skilled in the art enable this vanishing point to be determined. When the vehicle is approaching a bend, as in this example in FIG. 4b, the upper area 41b presents an offset 47b compared to the bottom area 42b. This offset 47b depends on the steering wheel angle and/or depends on the curvature of the road as defined by a navigation system.

The second area 42b corresponds to the bottom of the window. It is centered around the vanishing point 44b, 45b. This vanishing point is, for example, determined according to the road marking lines 46b, 46b. Other methods for determining a vanishing point, however, are well-known by the person skilled in the art.

The third area 43b corresponds to the intermediate area. It is arranged so as to ensure a transition between the first and second areas 41b, 42b. It thus extends in an oblique way to ensure continuity between these first and second horizontally offset areas when the vehicle is approaching a curve.

Advantageously, the vertical positioning of the limits between the various areas is carried out according to data relating to pitching of the vehicle and/or around the vanishing point 44b (steps 305, 306, 307—FIG. 3).

Preferably, contours are detected in the image (step 311—FIG. 3). This detection of contours can be implemented by one of the methods known by the person skilled in the art such as the Canny, Sobel, Prewitt, Roberts or Zero-cross methods. The detection of contours is aimed at identifying the non-homogeneous parts of the image. These parts generally reflect the presence of an object such as a tree, vehicle, road marking line, lamp post etc. Pixels belonging to contours are identified and removed from the subsequent steps.

Detection of contours thus improves the homogeneity of the region of interest and reduces the time necessary for defining and selecting the segments.

Pixels defining the end of an area of the search window are also identified. In the examples illustrated, the end of an area is delimited by the edges (21, 24—FIGS. 2a, 2b).

In another step, which is characteristic of the invention, the lines of each area are divided into segments. These segments are formed by "growing" the pixels (steps 312, 313, 314—FIG. 3).

The minimum size and maximum size of each segment are preset. These sizes correspond, respectively, to a minimum and maximum number of pixels per segment.

In order to form a segment, a pixel of the line $L_i$ is considered, pixels that are consecutive and pertaining to this same line $L_i$ are associated with this pixel until an end pixel of the segment $S_j$ is encountered. This end pixel is identified when a preset number of pixels corresponding to the maximum size of the segment is reached or when a pixel forming a contour or forming an area end is encountered. Thus, each segment is formed by incrementing the pixels, then a test relating to the maximum number of pixels, detection of a contour or an area end is carried out.

Figure 5:
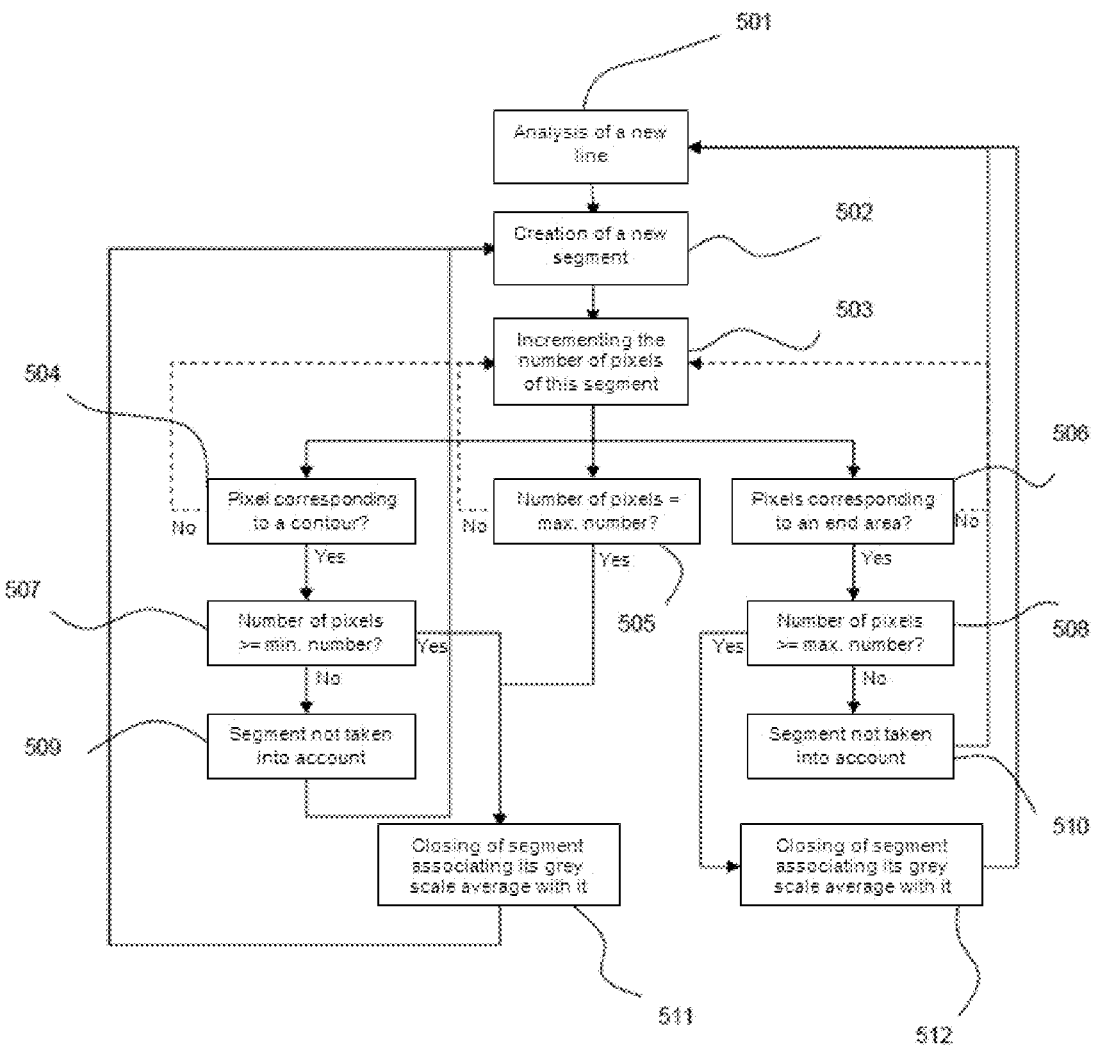
FIG. 5 is a diagram illustrating an example of an algorithm for defining the segments.

Dividing a line into segments thus follows the algorithm schematized in FIG. 5.

At step 501, the system according to the invention triggers the analysis of a new line. A new segment is then created starting from a first pixel (step 502). Another pixel, which is on this same line and adjacent to it, is associated with this pixel. It is determined if this other pixel corresponds to a contour (step 504) or to an area end (step 506) or enables this segment to reach its maximum number of pixels (step 505).

In the negative, the segment is incremented by an additional pixel (step 503) and the preceding checks of steps 504 to 506 are repeated.

When one of these checks is positive, that is to say, when the pixel that is added corresponds to a contour or delimits an area end or brings the number of pixels in this segment to the preset maximum, then incrementing the pixels stops. If the pixel incremented corresponds to a contour, this contour pixel is removed from the segment and the end of this segment is defined by the preceding pixel.

In addition, it is determined if this pixel exhibits a length greater than the preset minimum length, that is to say, if the minimum number of pixels has been reached for this segment (steps 507, 508).

In the negative, that is to say, if the minimum size of the segment has not been reached, then this segment is not taken into account (steps 509, 510) and a new segment is created. This new segment will be able to have, as a starting point, a pixel of the same line situated outside the contour that is detected and defining the end of the preceding segment. This new segment will be able to have, as a starting point, the following pixel if the preceding segment has reached a maximum size. If an area end is detected when the preceding segment is being divided, the starting pixel of the following segment is identified on the following line.

In the affirmative, that is to say, the segment has a size greater than the minimum size, then this segment is closed (steps 511, 512). The last pixel that is processed thus corresponds to a segment end.

Figure 6:
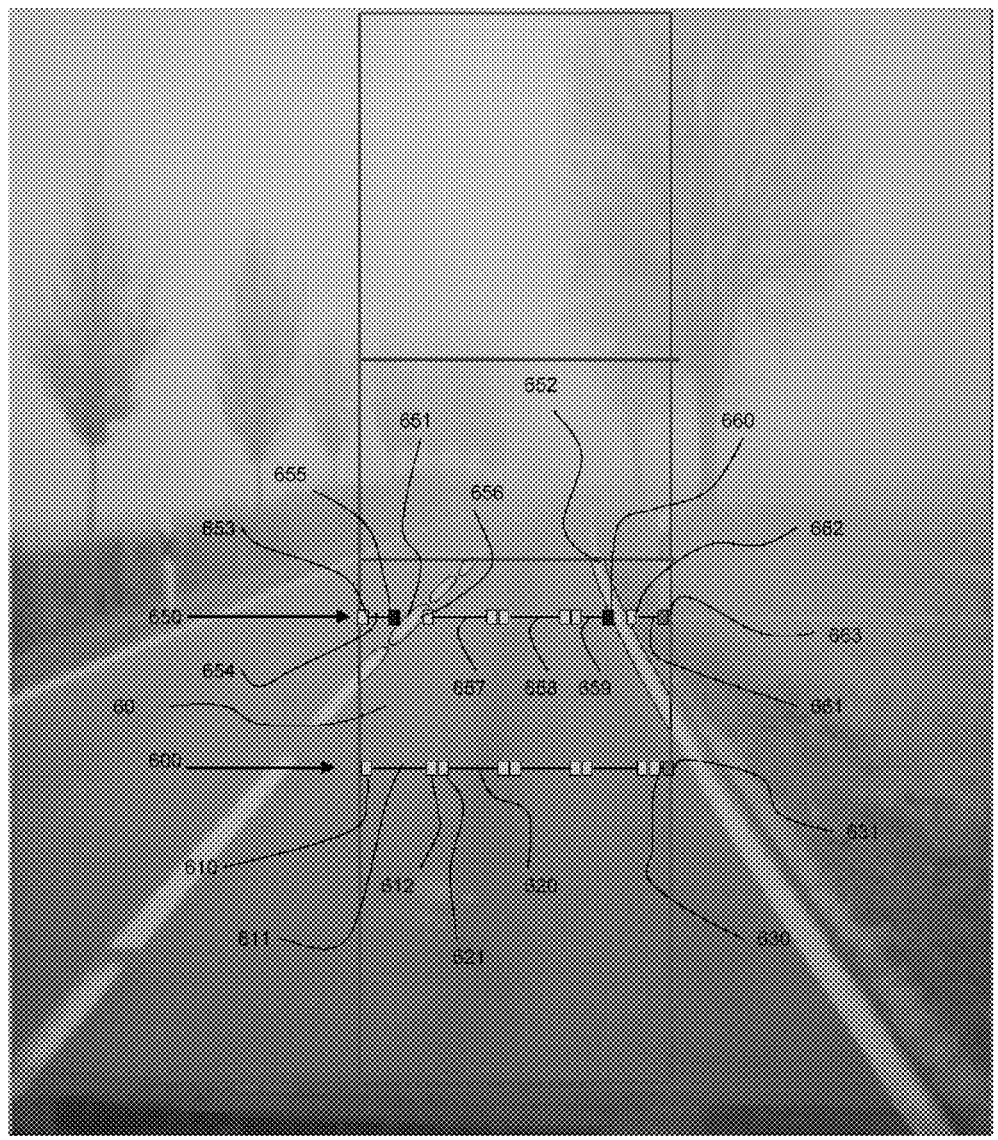
FIG. 6 illustrates an example for defining segments according to the invention.

FIG. 6 illustrates such a segmentation. In this figure the bottom area 60 shows two lines 600, 650 which are divided into a plurality of segments. Line 600 does not comprise a pixel forming a contour. The first pixel 610 of the first segment 611 is identified as the segment-starting pixel. By incrementation, this first pixel 610 extends on this line 600 from pixel to pixel until a maximum number of pixels is reached. The pixel 612 bringing this number to the preset maximum is identified as the segment-end pixel 612.

The following pixel 621 on the line is identified as a subsequent segment-starting pixel 620. The adjacent pixels are associated with it to form this other segment 620. At the end of the line, pixel 631 defining the area end is detected and stops the last segment 630. If this last segment 630 has a size greater than the minimum size, then it is preserved otherwise it is removed from the remainder of the processing.

Line 650 comprises contours corresponding to a discontinuous road marking 651 in the middle of the road and to a continuous road marking 652 at the edge of the road. These contours are identified by the processing system (step 311—FIG. 3). First pixel 653 defines the beginning of a first segment 654 for this line 650. By incrementation, the adjacent pixels are incorporated in this first segment 654 until reaching the pixel 655 adjacent to a pixel of the contour 651. Segment 654 is then stopped. The minimum number of pixels for this first segment 654 is then checked. The subsequent pixel 656 which can be selected at steps 502,503 is automatically a pixel situated outside the contour 651, since all the pixels inside the contour have been removed from processing. This subsequent pixel 656 thus defines the beginning of a second segment 657. The preceding steps are repeated. A plurality of segments 657, 658 of maximum size and a segment 659 of a size less than the maximum size and whose end is defined by a pixel 660 adjacent to contour 652 are obtained between the two contours 651, 652. For starting, segment 661 has a pixel 662 delimiting the contour 652 and, for ending, a pixel 663 delimiting the area end 60.

Thus, a plurality of segments is obtained for each line that is analyzed. The grey scale average is calculated for each segment. Preferably, this calculation is performed directly when the segment has been finally defined. The grey scale average corresponds to the sum of the grey levels of each pixel forming a segment related to the number of pixels of this segment. Thus, a kind of map of the segments likely to be incorporated in the region of interest is created.

A following step according to the invention consists in selecting from among all the segments that are defined those which will form the region of interest. This selection of segments is carried out for each area (steps 315, 316 and 317—FIG. 3). For this purpose, several methods of selection can be implemented.

The following method has proved to be particularly advantageous. The difference between the grey scale average of each NVGaverage(Sj) segment and the grey scale average of the preceding line NVGaverage($L_{i-1}$) are calculated. The grey scale average of the preceding line NVGaverage($L_{i-1}$) corresponds to the mean grey scale average of the selected segments of the preceding line, that is to say, the sum of the average grey scales of each segment selected in this line, divided by the number of segments selected in this line. It is determined if this difference is comprised in the interval [S; S'] where S and S' are preset thresholds. It can also be directly determined if the grey scale average of the segments for which the selection is performed is comprised in the interval [NVGaverage($L_{i-1}$)–S; NVGaverage($L_{i-1}$)+S]. S and S' can be defined based on a series of test images.

Particular care must be taken to ensure these thresholds are sufficiently tolerant to permit the change from one line to another according to progressive and natural degradation in the contrast of the image. Also, care must be taken to ensure these thresholds are sufficiently selective so as not to retain the segments situated on the portions of images, which correspond to objects appearing in the form of blurred texture. These objects are blurred in particular by fog or poor luminosity. They are, for example, trees, shadows, lamp posts, vehicles, bridges etc.

In the existing methods, these blurred objects are very often the cause of significant errors since they are not identified by the contour detection or region growing methods and disturb the homogeneity of the region of interest.

With the method according to the invention detection of contours allows pixels inducing a disturbance in the search window and resulting in degradation of the homogeneity of the region of interest to be eliminated from the outset.

Other methods for selecting the segments can be considered. It can be provided, for example, that only the segment having the highest grey scale average is selected for each line. Preferably, this method is applied in the first area corresponding to the top of the image.

An important advantage of segmenting the search window into various areas consists in being able to allot specific rules to each area in order to define or select the segments. Thus, the minimum and maximum sizes of the segments can be made to vary according to the area. Therefore, the segmenting precision and the time required for processing can be made to vary. By increasing the maximum size of the segments, the number of segments per line is reduced and the time required for selecting the segments is shortened.

Advantageously, each line of pixels is analyzed. It is also possible, for one or more areas, to choose to analyze only certain lines.

Segmenting the search window into a plurality of areas also enables different rules of selection to be applied according to the areas. For the intermediate area and for the bottom area, the method of selection described previously and relying on comparing the grey scale average of a NVGaverage($S_j$) segment with an interval can be provided for example; and for the top area the method described previously and consisting in retaining only the segment having the highest grey scale average NVGaverage($S_j$) in a line can be provided.

Segmenting into areas also enables these various areas to be processed simultaneously, in order to reduce the time required for determining the region of interest.

A next step of the method according to the invention consists in amalgamating all the segments selected during the preceding step (step 318—FIG. 3). Amalgamation of these segments forms a region of interest (step 319—FIG. 3).

Figure 7:
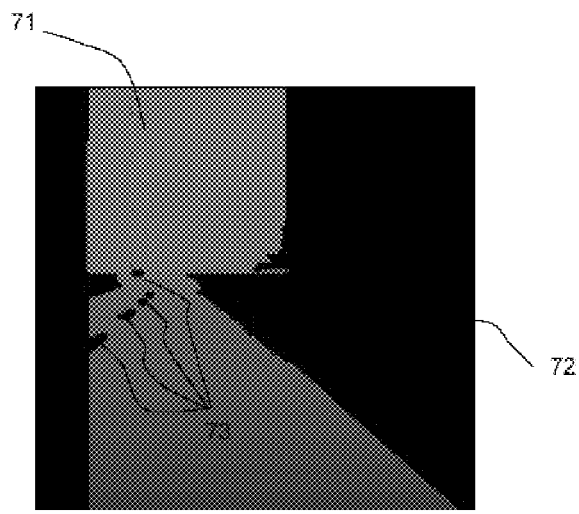
FIG. 7 is an example of a region of interest obtained by implementing the invention.

FIG. 7 illustrates an example of the region of interest 71 obtained according to the invention for an image 72 including objects such as road marking lines 73. The detection of contours and the method of segment growing allow, in the bottom window, a region of interest 71 to be defined while eliminating the road marking lines 73 from the middle of the road and the edges which may contain trees or textures which disturb the calculation of the luminance profile curve. Thus, a region of interest 71 having good homogeneity is obtained. It is then easy, for this region of interest, to establish a luminance profile with only one inflection point and to evaluate the visibility distance precisely. Moreover, this region of interest is obtained without requiring significant processing resources. In particular, the method according to the invention does not impose a vicinity constraint with regard to the pixels, unlike the methods of region growing which have proved extravagant in terms of the resources required for processing.

Advantageously, the region of interest obtained with the invention and a region of interest obtained with another method are amalgamated or compared. This enables the relevance of the region of interest to be enhanced and the degree of confidence in the region of interest obtained according to the invention to be increased.

A non-restrictive exemplary embodiment will now be described. In this example, the methods schematized in FIGS. 1, 3 and 5 in particular are applied.

For detecting contours (step 311—FIG. 3), the Canny method known by the person skilled in the art is used (see in particular the document [Deriche, 1987] Deriche, R. (1987). "Using Canny's criteria to derive an optimal edge detector recursively implemented".)

The window is divided into three areas. To implement the Canny method, a low threshold of 40 and a high threshold of 60 are allotted to the bottom area and to the intermediate area. A low threshold of 60 and a low threshold of 100 are allotted to the top area.

During selection of the segments (steps 315 to 317—FIG. 3), the following method is applied to the bottom areas and to the intermediate area: if the grey scale average of the segment considered is comprised in the interval [NVGaverage($L_{i-1}$)−S; NVGaverage($L_{i-1}$)+S'] with S=5 and S'=20 and NVGaverage $L_{i-1}$=mean grey scale averages of the segments selected from the preceding line; then this segment is selected. Otherwise, this segment is excluded from the region of interest. For the top area, only the segment having the highest grey scale average is retained for each line.

Figure 8:
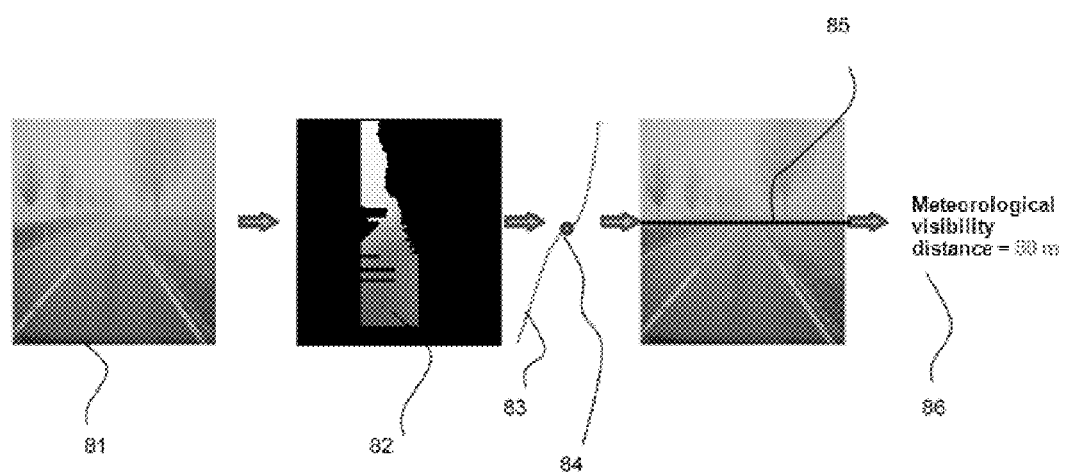
FIG. 8 illustrates another exemplary embodiment of the invention.

The segments selected in this way are amalgamated and the result illustrated in FIG. 8 is obtained.

On the basis of image 81, a homogenous region of interest 82 is determined. All the objects tending to degrade the homogeneity of the region of interest 82 (trees, road marking lines etc.) are, in fact, eliminated from this region of interest. A luminance profile 83 having only one inflection point 84 is then deduced from the region of interest. Based on this inflection point, the horizon line 85 is then precisely evaluated and a visibility distance 86 is derived from it.

The invention is not limited to the embodiments described but extends to any embodiment conforming to the essence of the invention.

While the method herein described, and the forms of apparatus for carrying this method into effect, constitute preferred embodiments of this invention, it is to be understood that the invention is not limited to this precise method and forms of apparatus, and that changes may be made in either without departing from the scope of the invention, which is defined in the appended claims.

What is claimed is:

1. A method for determining a region of interest in an image, this method being implemented in a road vehicle, said method comprising the following steps:
a plurality of lines $L_{i\ i=1,\ldots,n}$ formed by pixels is defined in the image;
in each line $L_i$, a plurality of segments $S_{j\ j=1,\ldots,m}$ constituted by pixels is defined;
a luminance level NVG($S_j$) is calculated for each segment $S_j$ based on the luminance of the pixels constituting this segment $S_j$;
depending on this luminance level NVG(Sj), the segment $S_j$ is selected or excluded from the region of interest; and
the region of interest is obtained by amalgamating all the segments selected for each line;
wherein the segment $S_j$ is excluded from the region of interest if the length of this segment $S_j$ is less than a predetermined minimum length.

2. The method according to claim 1, wherein the luminance level NVG($S_j$) is an average luminance level NVGaverage($S_j$) corresponding to the average luminance of each pixel of this segment $S_j$.

3. The method according to claim 2, wherein the following steps are carried out to determine if the $S_j$ segment is selected or not:
it is determined if the luminance level NVG($S_j$) of this segment is comprised in the interval [NVGaverage($L_{i-1}$)−S; NVGaverage($L_{i-1}$)+S'] with S and S' being preset thresholds and NVGaverage($L_{i-1}$) being the luminance level of one or more other adjacent lines;
if NVG($S_j$) is comprised in this interval, then the segment $S_j$ is selected; and
if NVG($S_j$) is not comprised in this interval, then this segment $S_j$ is excluded from the region of interest.

4. The method according to claim 2, wherein the definition of at least one segment $S_j$ of a line $L_i$ comprises the following steps: a pixel of the line $L_i$ is considered, the segment $S_j$ is constituted by incrementing this pixel of the pixels that are consecutive and pertaining to this same line $L_i$ until a predetermined maximum number of pixels is reached.

5. The method according to claim 1, wherein the following steps are carried out to determine if the $S_j$ segment is selected or not:
it is determined if the luminance level NVG($S_j$) of this segment is comprised in the interval [NVGaverage($L_{i-1}$)−S; NVGaverage($L_{i-1}$)+S'] with S and S' being preset thresholds and NVGaverage($L_{i-1}$) being the luminance level of one or more other adjacent lines;

if NVG($S_j$) is comprised in this interval, then the segment $S_j$ is selected; and if NVG($S_j$) is not comprised in this interval, then this segment $S_j$ is excluded from the region of interest.

6. The method according to claim 5, wherein the definition of at least one segment $S_j$ of a line $L_i$ comprises the following steps: a pixel of the line $L_i$ is considered, the segment $S_j$ is constituted by incrementing this pixel of the pixels that are consecutive and pertaining to this same line $L_i$ until a predetermined maximum number of pixels is reached.

7. The method according to claim 1, wherein the definition of at least one segment $S_j$ of a line $L_i$, comprises the following steps: a pixel of the line $L_i$ is considered, the segment $S_j$ is constituted by incrementing this pixel of the pixels that are consecutive and pertaining to this same line $L_i$ until a predetermined maximum number of pixels is reached.

8. The method according to claim 7 wherein, prior to defining the segment $S_j$, contours are searched by a contour detecting method, and wherein incrementing of the segment $S_j$ is stopped and this segment $S_j$ is closed if the pixel incremented forms a contour.

9. The method according to claim 1, wherein a search window, inside which the plurality of lines $L_i$ is defined, is isolated in the image.

10. The method according to claim 9, wherein the search window is segmented into a plurality of areas and specific rules concerning the definition of the segments $S_j$ and/or of the lines $L_i$ are allotted to each area.

11. The method according to claim 10, wherein the search window comprises at least one first area and one second area respectively positioned horizontally around a first and a second point of interest in the image.

12. The method according to claim 11, wherein the method is implemented in a road vehicle and at least one point of interest is determined as being a vanishing point from a system for detecting a vanishing point based on a steering wheel angle of the vehicle and/or from data generated by a navigation system and/or from a system for detecting road marking lines.

13. A system for determining a region of interest in an image, said system comprising a device for acquiring an image and means of processing arranged to implement the method according to claim 1.

14. A method for determining a region of interest in an image, this method being implemented in a road vehicle, said method comprising the following steps:

a plurality of lines $L_{i\ i=1,\ldots,n}$ formed by pixels is defined in the image;

in each line $L_i$, a plurality of segments $S_{j\ j=1,\ldots,m}$ constituted by pixels is defined;

a luminance level NVG($S_j$) is calculated for each segment $S_j$ based on the luminance of the pixels constituting this segment $S_j$;

depending on this luminance level NVG(Sj), the segment $S_j$ is selected or excluded from the region of interest; and the region of interest is obtained by amalgamating all the segments selected for each line;

wherein a search window, inside which the plurality of lines $L_i$ is defined, is located in the image;

wherein incrementing of the segment $S_j$ is stopped and this segment $S_j$ is closed if the pixel incremented corresponds to an edge of the search window.

15. The method according to claim 14, wherein the search window is segmented into a plurality of areas and specific rules concerning the definition of the segments $S_j$ and/or of the lines $L_i$ are allotted to each area.

16. A method for determining a region of interest in an image, this method being implemented in a road vehicle, said method comprising the following steps:

a plurality of lines $L_{i\ i=1,\ldots,n}$ formed by pixels is defined in the image;

in each line $L_i$, a plurality of segments $S_{j\ j=1,\ldots,m}$ constituted by pixels is defined;

a luminance level NVG($S_j$) is calculated for each segment $S_j$ based on the luminance of the pixels constituting this segment $S_j$;

depending on this luminance level NVG(Sj), the segment $S_j$ is selected or excluded from the region of interest; and the region of interest is obtained by amalgamating all the segments selected for each line;

wherein a search window, inside which the plurality of lines $L_i$ is defined, is isolated in the image;

wherein the search widow is segmented into a plurality of areas and specific rules concerning the definition of the segments $S_j$ and/or of the lines $L_i$ are allotted to each area;

wherein the search window comprises at least one first area and one second area respectively positioned horizontally around a first and a second point of interest in the image;

wherein the search window comprises a third area defined so as to ensure continuity between the first and second areas.

17. A method for determining a region of interest in an image, this method being implemented in a road vehicle, said method comprising the following steps:

a plurality of lines $L_{i\ i=1,\ldots,n}$ formed by pixels is defined in the image;

in each line $L_i$, a plurality of segments $S_{j\ j=1,\ldots,m}$ constituted by pixels is defined;

a luminance level NVG($S_j$) is calculated for each segment $S_j$ based on the luminance of the pixels constituting this segment $S_j$;

depending on this luminance level NVG(Sj), the segment $S_j$ is selected or excluded from the region of interest; and the region of interest is obtained by amalgamating all the segments selected for each line;

wherein a search window, inside which the plurality of lines $L_i$ is defined, is isolated in the image;

wherein the search widow is segmented into a plurality of areas and specific rules concerning the definition of the segments $S_j$ and/or of the lines $L_i$ are allotted to each area;

wherein the search window comprises at least one first area and one second area respectively positioned horizontally around a first and a second point of interest in the image;

wherein the search window comprises a third area defined so as to ensure continuity between the first and second areas;

wherein the search window is segmented so that the third area corresponds in the image to a transition between the road and the sky;

wherein the limits between the areas of the search window are vertically positioned according to data relating to pitching of the vehicle or so that the third area is vertically centered around a vanishing point of the image.

18. A method for determining a region of interest in an image, this method being implemented in a road vehicle, said method comprising the following steps:

a plurality of lines $L_{i\ i=1,\ldots,n}$ formed by pixels is defined in the image;

in each line $L_i$, a plurality of segments $S_{j\,j=1,\ldots,m}$ constituted by pixels is defined;

a luminance level $NVG(S_j)$ is calculated for each segment $S_j$ based on the luminance of the pixels constituting this segment $S_j$;

depending on this luminance level NVG(Sj), the segment $S_j$ is selected or excluded from the region of interest; and the region of interest is obtained by amalgamating all the segments selected for each line;

wherein the search widow is segmented into a plurality of areas and specific rules concerning the definition of the segments $S_j$ and/or of the lines $L_i$ are allotted to each area;

wherein the search window comprises at least one first area and one second area respectively positioned horizontally around a first and a second point of interest in the image;

wherein the method is implemented in a road vehicle and at least one point of interest is determined as being a vanishing point from a system for detecting a vanishing point based on a steering wheel angle of the vehicle and/or from data generated by a navigation system and/or from a system for detecting road marking lines;

wherein the search window comprises a third area defined so as to ensure continuity between the first and second areas.

19. The method according to claim 18, wherein the search window is segmented so that the third area corresponds in the image to a transition between the road and the sky.

20. The method according to claim 18, wherein the limits between the areas of the search window are vertically positioned according to data relating to pitching of the vehicle or so that the third area is vertically centered around a vanishing point of the image.

21. A system for aiding a driver to drive a road vehicle comprising:

means for defining a plurality of lines $L_{i\,i=1,\ldots,n}$ formed by pixels is defined in the image;

means for defining in each line $L_i$, a plurality of segments $S_{j\,j=1,\ldots,m}$ constituted by pixels;

means for collecting a luminance level $NVG(S_j)$ for each segment $S_j$ based on the luminance of the pixels constituting this segment $S_j$;

means for selecting or excluding the segment $S_j$ from the region of interest in response to this luminance level NVG(Sj); and means for amalgamating all the segments selected for each line to obtain the region of interest;

wherein the segment $S_j$ is excluded from the region of interest if the length of this segment $S_j$ is less than a predetermined minimum length.

22. The system according to claim 21, wherein the luminance level $NVG(S_j)$ is an average luminance level NVGaverage($S_j$) corresponding to the average luminance of each pixel of this segment $S_j$.

23. The system according to claim 21, wherein the following steps are carried out to determine if the $S_j$ segment is selected or not:

it is determined if the luminance level $NVG(S_j)$ of this segment is comprised in the interval [NVGaverage($L_{i-1}$)−S; NVGaverage($L_{i-1}$)+S'] with S and S' being preset thresholds and NVGaverage($L_{i-1}$) being the luminance level of one or more other adjacent lines;

if $NVG(S_j)$ is comprised in this interval, then the segment $S_j$ is selected; and if $NVG(S_j)$ is not comprised in this interval, then this segment $S_j$ is excluded from the region of interest.

24. A system for aiding a driver to drive a road vehicle wherein said system comprises a processor programmed with a computer program having one or more sequences of instructions that:

defines a plurality of lines $L_{i\,i=1\,\ldots\,n}$ formed by pixels defined in the image;

defines in each line $L_i$, a plurality of segments $S_{j\,j=1\,\ldots\,m}$ constituted by pixels;

collects a luminance level $NVG(S_j)$ for each segment $S_j$ based on the luminance of the pixels constituting this segment $S_j$;

selects or excluding the segment $S_j$ from the region of interest in response to this luminance level $NVG(S_j)$; and amalgamates all the segments selected for each line to obtain the region of interest;

wherein the segment $S_j$ is excluded from the region of interest if the length of this segment $S_j$ is less than a predetermined minimum length.

25. The system according to claim 24, wherein the luminance level $NVG(S_j)$ is an average luminance level NVGaverage($S_j$) corresponding to the average luminance of each pixel of this segment $S_j$.

26. The system according to claim 24, wherein the following steps are carried out to determine if the $S_j$ segment is selected or not:

it is determined if the luminance level $NVG(S_j)$ of this segment is comprised in the interval [NVGaverage($L_{i-1}$)−S; NVGaverage($L_{i-1}$)+S'] with S and S' being preset thresholds and NVGaverage($L_{i-1}$) being the luminance level of one or more other adjacent lines;

if $NVG(S_j)$ is comprised in this interval, then the segment $S_j$ is selected; and if $NVG(S_j)$ is not comprised in this interval, then this segment $S_j$ is excluded from the region of interest.

* * * * *